(12) United States Patent
Purcell

(10) Patent No.: US 8,303,615 B2
(45) Date of Patent: Nov. 6, 2012

(54) LANCET-EJECT MECHANISM

(75) Inventor: D. Glenn Purcell, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 130 days.

(21) Appl. No.: 12/530,654

(22) PCT Filed: Mar. 12, 2007

(86) PCT No.: PCT/US2007/006225
§ 371 (c)(1),
(2), (4) Date: Feb. 2, 2010

(87) PCT Pub. No.: WO2008/111936
PCT Pub. Date: Sep. 18, 2008

(65) Prior Publication Data
US 2010/0179579 A1   Jul. 15, 2010

(51) Int. Cl.
*A61B 5/151* (2006.01)
(52) U.S. Cl. ........................ 606/182; 606/181
(58) Field of Classification Search ............... 606/181, 606/182
See application file for complete search history.

(56) References Cited

U.S. PATENT DOCUMENTS

| | | | |
|---|---|---|---|
| 3,797,488 | A | 3/1974 | Hurschman et al. |
| 4,203,446 | A | 5/1980 | Hofert et al. |
| 4,442,836 | A | 4/1984 | Meinecke et al. |
| 4,449,529 | A | 5/1984 | Burns et al. |
| 4,469,110 | A | 9/1984 | Slama et al. |
| 4,517,978 | A | 5/1985 | Levin et al. |
| 4,553,541 | A | 11/1985 | Burns |
| 4,627,445 | A | 12/1986 | Garcia et al. |
| 4,637,403 | A | 1/1987 | Garcia et al. |
| 4,735,203 | A | 4/1988 | Ryder et al. |
| D297,459 | S | 8/1988 | Heiland et al. |

(Continued)

FOREIGN PATENT DOCUMENTS
DE        459 483        5/1928
(Continued)

OTHER PUBLICATIONS

International Search Report for PCT/US2007/006225 dated Nov. 1, 2008, (5 pages).

*Primary Examiner* — Kathleen Sonnett
*Assistant Examiner* — Sarah Webb
(74) *Attorney, Agent, or Firm* — Nixon Peabody LLP

(57) ABSTRACT

A lancing device comprises a main housing, a movable housing and a pushbutton. The main housing encloses a portion of a lancing mechanism. The lancing mechanism includes a lancet holder attached to a shaft. The lancet holder receives a lancet and has a slot formed therein. The lancing mechanism moves between a rest position, a cocked position, and a puncture position. The movable housing is adjacent to the main housing. The movable housing moves from a rest position to a cocking position and a lancet-release position. The pushbutton allows the lancing mechanism to move from the cocked position to the puncture position upon depression of the pushbutton. The pushbutton includes a lancet-release tab that extends into the slot formed in the lancet holder and engages the lancet. The lancet is released from the lancet holder in response to the continued depression of the pushbutton and the movable housing is moved from the rest position to the lancet-release position.

15 Claims, 9 Drawing Sheets

U.S. PATENT DOCUMENTS

| | | |
|---|---|---|
| 4,787,398 A | 11/1988 | Garcia et al. |
| RE32,922 E | 5/1989 | Levin et al. |
| 4,924,879 A | 5/1990 | O'Brien |
| 4,976,724 A | 12/1990 | Nieto et al. |
| 4,990,154 A | 2/1991 | Brown et al. |
| 5,074,872 A | 12/1991 | Brown et al. |
| D332,490 S | 1/1993 | Brown et al. |
| 5,196,025 A | 3/1993 | Ranalletta et al. |
| 5,231,993 A | 8/1993 | Haber et al. |
| 5,267,963 A | 12/1993 | Bachynsky |
| 5,279,294 A | 1/1994 | Anderson et al. |
| 5,304,193 A | 4/1994 | Zhadanov |
| 5,318,583 A | 6/1994 | Rabenau et al. |
| 5,318,584 A | 6/1994 | Lange et al. |
| 5,320,607 A | 6/1994 | Ishibashi |
| 5,324,303 A | 6/1994 | Strong et al. |
| 5,350,392 A | 9/1994 | Purcell et al. |
| 5,527,334 A | 6/1996 | Kanner et al. |
| 5,554,166 A | 9/1996 | Lange et al. |
| 5,575,777 A | 11/1996 | Cover et al. |
| 5,628,764 A | 5/1997 | Schraga |
| D393,716 S | 4/1998 | Brenneman et al. |
| D393,717 S | 4/1998 | Brenneman et al. |
| 5,741,288 A | 4/1998 | Rife |
| 5,797,942 A | 8/1998 | Schraga |
| 5,868,772 A | 2/1999 | LeVaughn et al. |
| 5,871,494 A | 2/1999 | Simons et al. |
| 5,916,230 A | 6/1999 | Brenneman et al. |
| 5,951,492 A | 9/1999 | Douglas et al. |
| 5,951,493 A | 9/1999 | Douglas et al. |
| 5,954,738 A | 9/1999 | LeVaughn et al. |
| 6,022,366 A | 2/2000 | Schraga |
| 6,045,567 A | 4/2000 | Taylor et al. |
| 6,048,352 A | 4/2000 | Douglas et al. |
| 6,050,977 A | 4/2000 | Adams et al. |
| 6,090,078 A | 7/2000 | Erskine et al. |
| 6,090,124 A | 7/2000 | Weekes et al. |
| 6,093,156 A | 7/2000 | Cunningham et al. |
| 6,099,484 A | 8/2000 | Douglas et al. |
| 6,152,942 A | 11/2000 | Brenneman et al. |
| 6,156,051 A | 12/2000 | Schraga et al. |
| 6,168,606 B1 | 1/2001 | Levin et al. |
| 6,197,040 B1 | 3/2001 | LeVaughn et al. |
| 6,210,421 B1 | 4/2001 | Bocker |
| 6,231,531 B1 | 5/2001 | Lum et al. |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,364,889 B1 | 4/2002 | Kheiri et al. |
| 6,379,317 B1 | 4/2002 | Kintzing et al. |
| 6,409,740 B1 | 6/2002 | Kuhr et al. |
| 6,419,661 B1 | 7/2002 | Kuhr et al. |
| 6,432,120 B1 | 8/2002 | Teo |
| 6,451,040 B1 | 9/2002 | Purcell |
| 6,514,270 B1 | 2/2003 | Schraga |
| 6,537,292 B1 | 3/2003 | Lee |
| 6,561,989 B2 | 5/2003 | Whitson et al. |
| 6,602,268 B2 | 8/2003 | Kuhr et al. |
| 6,607,543 B2 | 8/2003 | Purcell et al. |
| 6,749,618 B2 | 6/2004 | LeVaughn et al. |
| 6,752,817 B2 | 6/2004 | Flora et al. |
| 6,837,858 B2 | 1/2005 | Cunningham et al. |
| 7,144,404 B2 | 12/2006 | Whitson |
| 7,238,192 B2 | 7/2007 | List et al. |
| 7,273,484 B2 * | 9/2007 | Thoes et al. .................. 606/181 |
| 7,303,573 B2 | 12/2007 | D'Agostino |
| 2002/0022789 A1 | 2/2002 | Perez et al. |
| 2002/0087180 A1 | 7/2002 | Searle et al. |
| 2003/0171696 A1 | 9/2003 | Dosmann |
| 2003/0171699 A1 | 9/2003 | Brenneman |
| 2003/0187470 A1 | 10/2003 | Chelak et al. |
| 2003/0216767 A1 | 11/2003 | List et al. |
| 2004/0059256 A1 | 3/2004 | Perez |
| 2004/0248312 A1 | 12/2004 | Vreeke et al. |
| 2005/0085840 A1 | 4/2005 | Yi et al. |
| 2005/0090850 A1 | 4/2005 | Thoes et al. |
| 2005/0149090 A1 | 7/2005 | Morita et al. |
| 2006/0229652 A1 | 10/2006 | Iio et al. |
| 2006/0247670 A1 | 11/2006 | LeVaughn et al. |
| 2008/0140105 A1 | 6/2008 | Zhong et al. |
| 2008/0167673 A1 | 7/2008 | Zhong et al. |
| 2008/0195133 A1 | 8/2008 | Zhong et al. |

FOREIGN PATENT DOCUMENTS

| | | |
|---|---|---|
| EP | 0 115 388 | 8/1984 |
| EP | 0 204 892 | 12/1986 |
| EP | 0 569 124 A1 | 11/1993 |
| EP | 0 894 471 | 2/1999 |
| EP | 0 898 936 | 3/1999 |
| EP | 0 958 783 | 11/1999 |
| EP | 1 535 573 | 6/2005 |
| EP | 1 541 088 | 6/2005 |
| JP | 2000175889 | 6/2000 |
| WO | WO 02/100278 | 12/2002 |
| WO | WO 2004/103178 | 12/2004 |
| WO | WO 2005/001418 | 1/2005 |
| WO | WO 2005/046477 | 5/2005 |
| WO | WO 2005/077275 | 8/2005 |
| WO | WO 2005/011496 | 10/2005 |
| WO | WO 2006/031535 | 4/2006 |
| WO | WO 2006/096540 | 9/2006 |
| WO | WO 2006/096630 | 9/2006 |
| WO | WO 2006/107914 | 10/2006 |

* cited by examiner

LANCET-EJECT MECHANISM

CROSS-REFERENCE To RELATED APPLICATIONS

This application is a U.S. national stage of International Application No. PCT/US2007/006225, filed Mar. 12, 2007, which is hereby incorporated by reference herein in its entirety.

FIELD OF THE INVENTION

The present invention relates generally to diagnostic instruments and, more particularly, to a lancet-release mechanism for a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

Existing lancing devices require are potentially dangerous when—or are ineffective in—releasing the lancet. Typical two-handed operation requires that one hand hold the lancing device while the other hand removes the lancet. This is inconvenient to many users as the lancet is small, and may cause safety problems as the lancet could pierce the user's skin inadvertently. This can cause user pain and may also transmit diseases. Some lancet-release designs have complicated release mechanisms internally, such that if a user drops the lancing device, the release mechanism may jam and no longer eject the lancet from the lancing device.

It would be desirable to have a lancing device and a method for using a lancing device that address these issues.

SUMMARY OF THE INVENTION

According to one embodiment of the present invention, a lancing device is disclosed. The lancing device comprises a main housing, a movable housing, and a pushbutton. The main housing encloses a portion of a lancing mechanism including a lancet holder attached to a shaft. The lancet holder is adapted to receive a lancet and has a slot formed therein. The lancing mechanism is adapted to move between a rest position, a cocked position, and a puncture position. The movable housing is adjacent the main housing and is adapted to move from a rest position to a cocking position and a lancet-release position. The pushbutton is adapted to allow the lancing mechanism to move from the cocked position to the puncture position upon depression of the pushbutton in the general direction of the main housing. The pushbutton includes a lancet-release tab formed thereon. The lancet-release tab is adapted to extend into the slot formed in the lancet holder and engage the lancet. The lancet is released from the lancet holder in response to the continued depression of the pushbutton and the movable housing being moved from the rest position to the lancet-release position.

According to another embodiment of the present invention, a method of releasing a lancet from a lancing device is disclosed. The method comprises the act of providing a lancing device including (i) a main housing enclosing a lancet holder being adapted to receive the lancet, the lancet holder having a slot formed therein, (ii) a movable housing adjacent the main housing, the movable housing being adapted to move from a rest position to a cocking position and a lancet-release position, and (iii) a pushbutton having a lancet-release tab formed thereon, the lancet-release tab being adapted to extend into the slot formed in the lancet holder and engage the lancet. The method further comprises the act depressing the pushbutton in the general direction of the main housing resulting in the lancet-release tab entering the slot formed in the lancet holder. The method further comprises the act of moving the movable housing from the rest position to the lancet-release position, while the pushbutton remains depressed. The movement of the movable housing causes the lancet-release tab to engage the lancet and cause the lancet to release from the lancet holder.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a lancing device that is adapted to receive and release a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{1C}$, fructose, lactate, or bilirubin.

Figure 1:
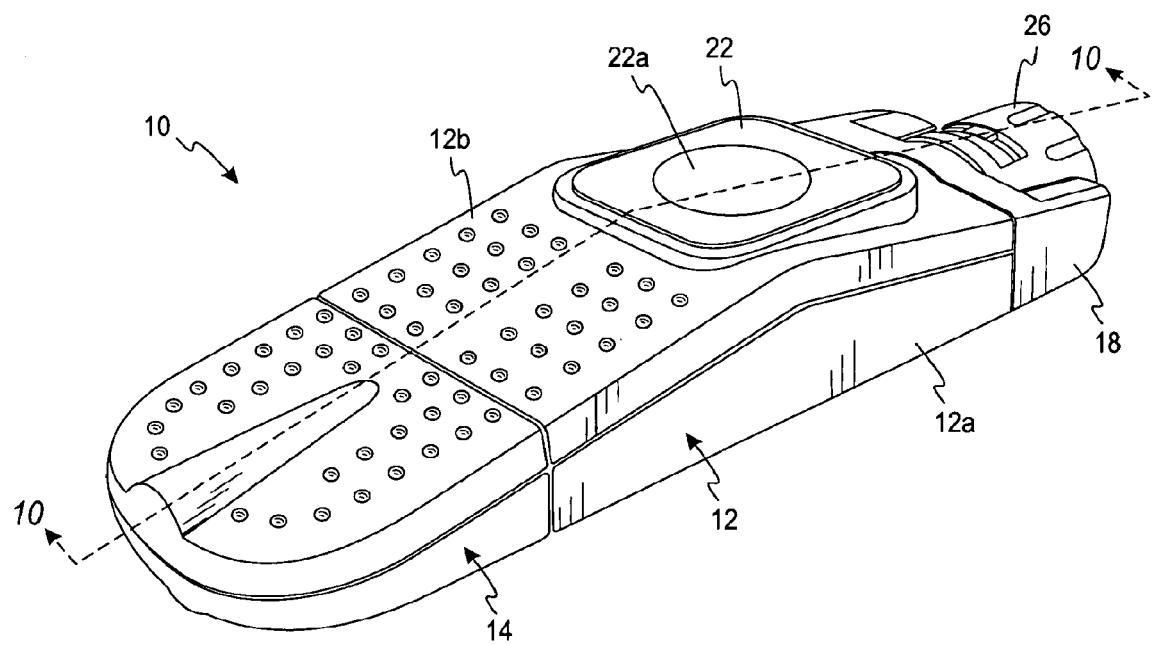
FIG. 1 is a perspective view of a lancing device and endcap, according to one embodiment of the present invention.
Figure 2:
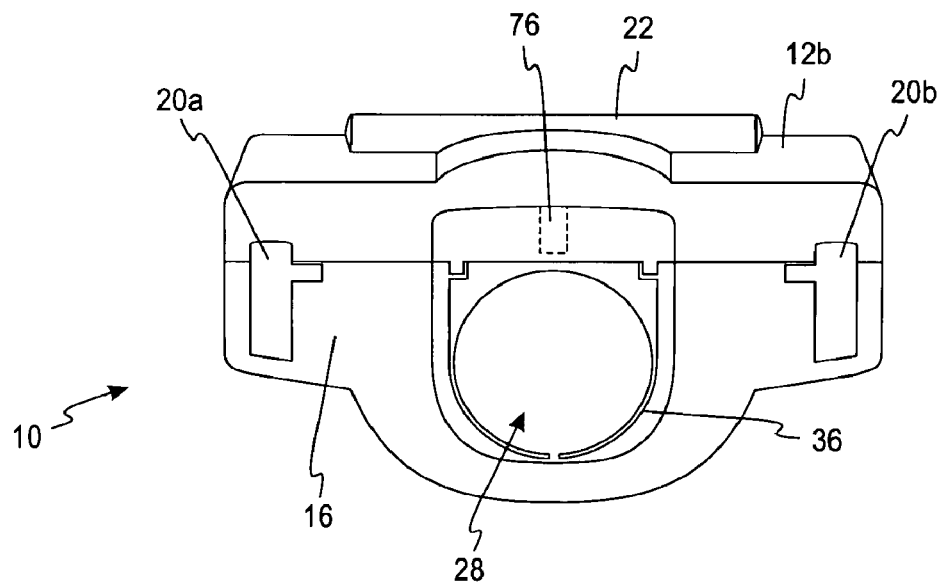
FIG. 2 is a front view of the lancing device of FIG. 1.
Figure 3:
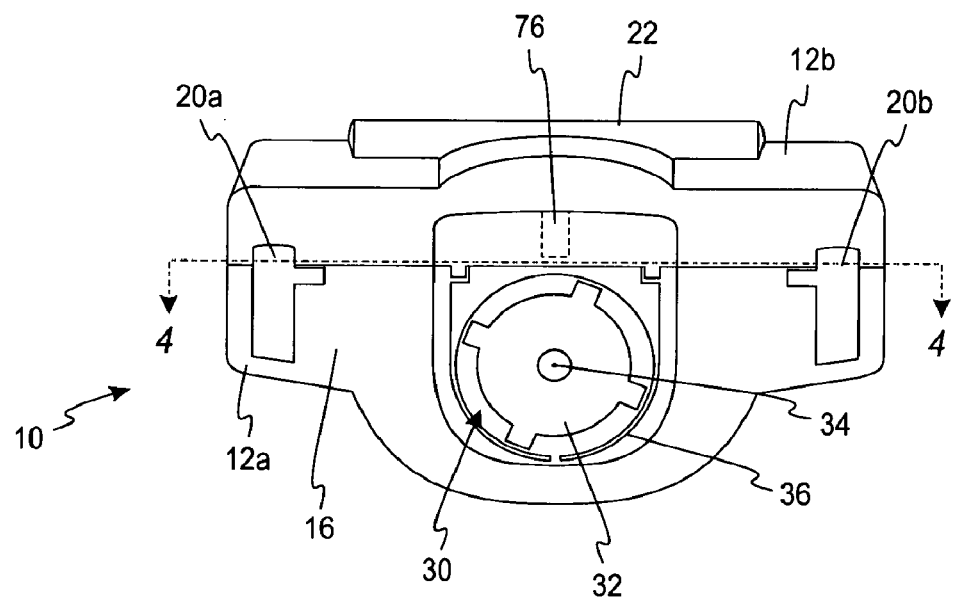
FIG. 3 is a front view of the lancing device of FIG. 1 with a lancet received therein.

Turning now to the drawings and initially to FIGS. 1-3, a lancing device 10 for obtaining a fluid sample from a test subject is illustrated, according to one embodiment of the present invention. The lancing device 10 has a main housing 12 with a movable housing 14 movable relative to the main housing 12. The main housing 12 includes a first main-housing portion 12a and a second main-housing portion 12b. The first and second main-housing portions 12a,b may be removably attachable or may be formed or molded as one permanently attached piece. An endcap support 16 is connected to the main housing 12 on the testing end of the lancing device 10. An endcap 18 may be removably attached to the endcap support 16. When attached, the endcap 18 is retained on the endcap support 16 by, for example, a pair of support arms 20a-b integrally formed with the endcap support 16.

Figure 8:
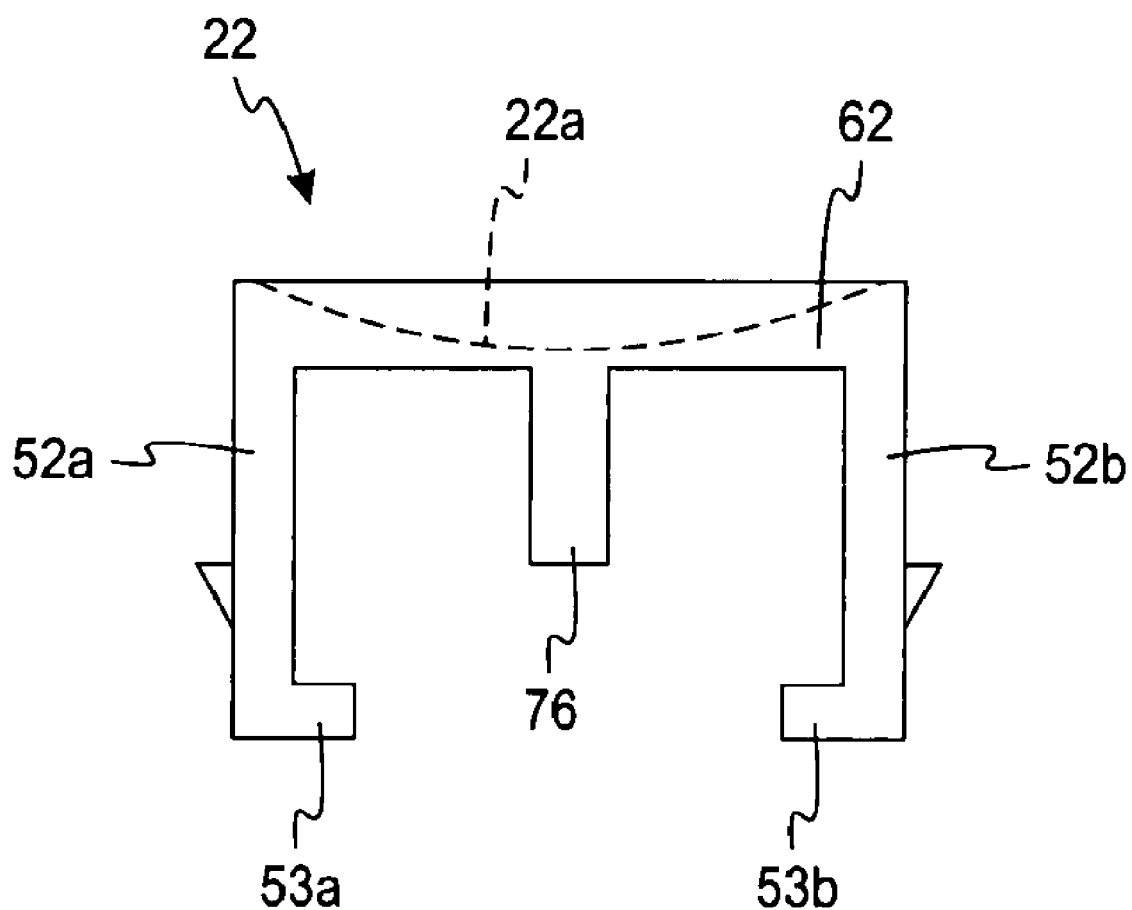
FIG. 8 is a front view of a pushbutton of the lancing device of FIG. 1, according to one embodiment of the present invention.

When used, the movable housing 14 is pulled away from the main housing 12 to move an internal lancing mechanism 24 (FIGS. 9a-b) to a cocked position, and then a pushbutton 22 (as best illustrated in FIG. 8) is depressed to actuate the lancing mechanism 24 so that a sharp-tipped lance 34 of a lancet 30 is forced through an aperture (not shown) formed in the endcap 18. The lancing device 10 may be provided with a number of different endcaps 18, each having a different width, to facilitate the formation of skin punctures of various depths. Alternatively, the endcap 18 may include an adjustable dial 26 for allowing punctures of different depths to be performed utilizing a single endcap 18.

FIGS. 2-3 illustrate an end view of the lancing device 10 with the endcap 18 removed. A lancet holder 36 includes a central, generally-cylindrical aperture 28 formed therein. The aperture 28 is adapted to receive the lancet 30, as illustrated in FIG. 3. The lancet 30 includes a lancet body 32 with the sharp-tipped lance 34 extending therefrom. The lance 34 may initially be enclosed within a protective cap 70 (FIG. 9) to protect a user from unintended punctures. Additionally, the protective cap 70 assists with preventing or inhibiting the lance 34 from being contaminated prior to use and also may be replaced after the use of the lance 34, prior to discarding the lancet 30.

Figure 4:
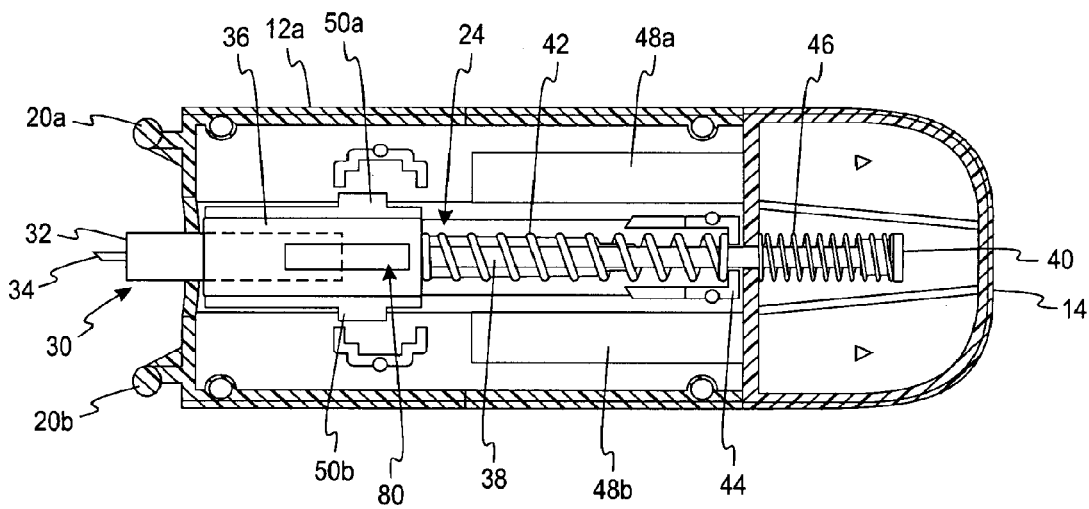
FIG. 4 is a cross-sectional view of the lancing device of FIG. 1 taken generally along line 4-4 of FIG. 3 with a lancet received therein, the lancing device being in a resting position.

Referring also to FIG. 4, a cross-sectional top view of the lancing device 10 in a resting position with the endcap 18 detached is illustrated. The lancet holder 36 is connected to an elongated shaft 38 by being integrally formed therewith. The shaft 38 has an retainer 40 that is supported within the movable housing 14. A drive spring 42 is disposed around the shaft 38 between the lancet holder 36 and a spring stop 44 integrally formed with the first main-housing portion 12a.

The movable housing 14 has a pair of elongated columns 48a,b integrally formed therewith. Each of the columns 48a,b extends into the main housing 12 through an aperture (not shown) formed in the first main-housing portion 12a. A secondary spring 46 is disposed around the shaft 38 within the movable housing 14. A first end of the secondary spring 46 is disposed against an internal surface of the movable housing 14 and a second end of the secondary spring 46 is disposed against the retainer 40 of the shaft 38. The secondary spring 46 is centrally located within the movable housing 14 along the longitudinal axis of the lancing device 10.

Figure 5:
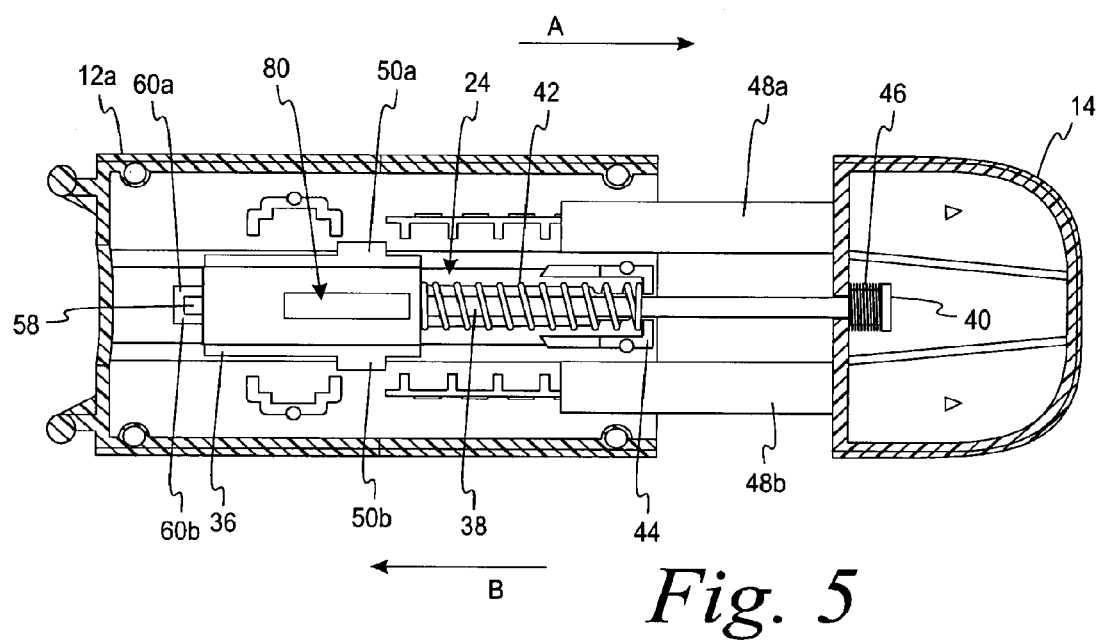
FIG. 5 is a cross-sectional view of the lancing device of FIG. 1 taken generally along line 4-4 of FIG. 3 in a cocking position.

FIG. 4 illustrates the interior of the lancing device 10 when the lancing device 10 is at rest. In this position, the lancet holder 36 is disposed in a rest position between a puncture position and a cocked position. In the rest position, both the drive spring 42 and the secondary spring 46 are substantially uncompressed and are in equilibrium with each other FIG. 5 illustrates the interior of the lancing device 10 (the lancet 30 is not shown) when the lancet holder 36 and movable housing 14 are in a cocking position in which the movable housing 14 has been pulled away from the main housing 12. In the cocking position, both the drive spring 42 and the secondary spring 46 are substantially compressed as the user moves the movable housing 14 away from the housing 12 in the direction of Arrow A.

Figure 6:
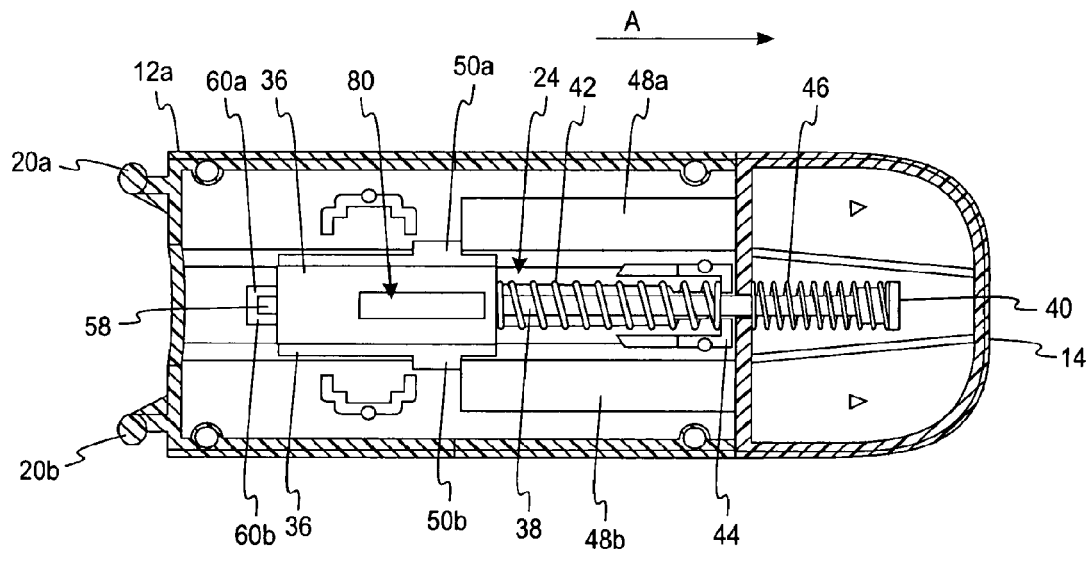
FIG. 6 is a cross-sectional view of the lancing device of FIG. 1 taken generally along line 4-4 of FIG. 3 in a cocked position.
Figure 7:
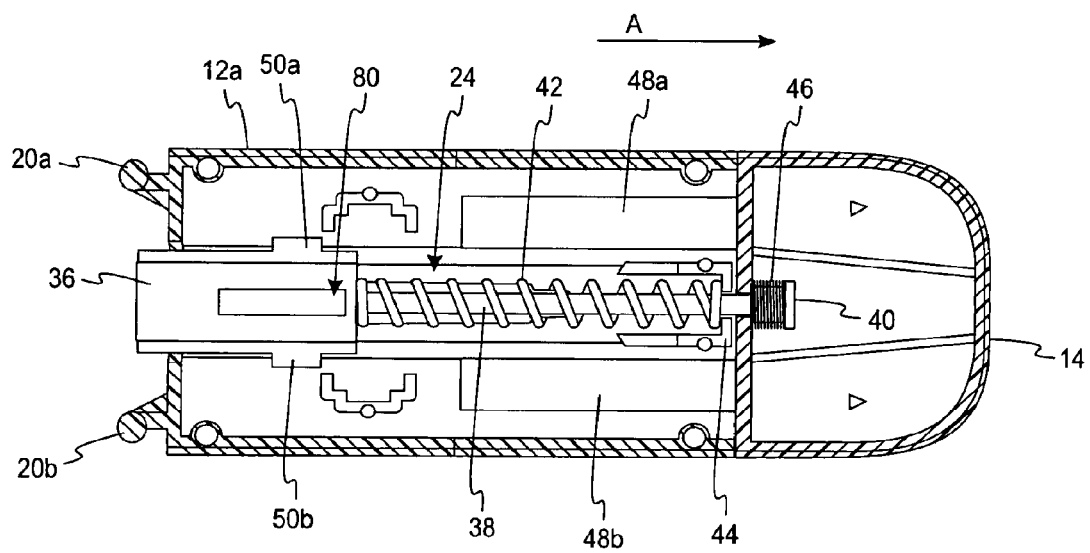
FIG. 7 is a cross-sectional view of the lancing device of FIG. 1 taken generally along line 4-4 of FIG. 3 in a puncture position.

Referring now to FIGS. 4-8, to move the lancet holder 36 from its rest position to its cocked position, the movable housing 14 is pulled away from the main housing 12 in the direction of Arrow A. The movable housing 14 continues to be pulled—against the force of the drive spring 42 and the secondary spring 46—until a plurality of angled stop members 50a,b formed on the lancet holder 36 move past (to the right of as illustrated in FIGS. 4-6) a plurality of catch arms 52a,b located on the pushbutton 22 (as best illustrated in FIG. 8). Each of the catch arms 52a,b has a respective end 53a,b adapted to engage the angled stop members 50a,b. The ends 53a,b of the catch arms 52a,b are angled opposite the angled stop members 50a,b, such that when the angled stop members 50a,b are moved in the direction of Arrow A they contact the ends 53a,b of the catch arms 52a,b. The movement of the angled stop members 50a,b forces the ends 53a,b of the catch arms 52a,b—as well as the attached pushbutton 22—in the direction of the first main housing portion 12a.

Once the angled stop members 50a,b have moved past the ends 53a,b of the catch arms 52a,b, a spring mechanism 82 (illustrated in FIGS. 10a-c)—located between the second main-housing portion 12b and the pushbutton 22—forces the catch arms 52a,b towards the first main-housing portion 12a. This movement causes the ends 53a,b of the catch arms 52a,b to engage the angled stop members 50a,b. In this position, movement of the lancet holder 36 in the direction of Arrow B (see FIGS. 4-7) due to the drive spring 42 is prevented. After the angled stop members 50a,b have been engaged, the user releases the movable housing 14 and allows the now compressed secondary spring 46 to force the movable housing 14 back to its initial position adjacent the main housing 12, as illustrated in FIG. 6. The lancing device 10 is now in its cocked position, wherein the drive spring 42 is substantially compressed, and the secondary spring 46 is substantially decompressed.

The lancet holder 36 is guided between its resting and cocked positions by a guide rib 56 (FIG. 9a) formed on a portion of the lancet holder 36. The guide rib 56 rides within a groove 58 (FIGS. 5-6 and FIGS. 10a-10c) formed between a pair of raised guide rails 60a,b (FIGS. 5-6) formed in an interior portion of the first main-housing portion 12a.

To perform a puncture on a test subject's skin, the endcap 18 is attached to the lancing device 10. The lancet holder 36 may be in the cocked position at the time the endcap 18 is attached or may be cocked once the endcap 18 has been removably attached to the endcap support 16. The endcap 18 is then placed firmly against the skin where the puncture is to be made, and the pushbutton 22 is depressed. Depressing the pushbutton 22 causes the catch arms 52a,b (FIG. 8)—integrally formed with the bottom of the pushbutton 22—to move toward the first main-housing portion 12a away from the lancet holder 36. Thus, the lancet holder 36 is no longer prevented from moving in the direction of Arrow B by the contact of the ends 53a,b of the catch arms 52a,b with the angled stop members 50a,b of the lancet holder 36. The spring mechanism 82 of FIGS. 10a-c—for example, one or more spring bars or an elastically deformable foam material—is formed on (or disposed between) the second main-housing portion 12b and the pushbutton 22 to bias the pushbutton 22 to its non-actuated position.

Upon release of the lancet holder 36 as described above, the drive spring 42 will force the lancet holder 36 in the direction of Arrow B until the sharp point of the lance 34 (FIG. 4) passes through the aperture (not shown) in the endcap 18 to make the puncture. As the lancet holder 36 moves in the direction of Arrow B, the attached shaft 38 also moves in the direction of Arrow B. The retainer 40 of the shaft 38 causes the secondary spring 46 to compress as the lancet holder 36 moves to the puncture position. As the lancing mechanism 24 reaches the puncture position (FIG. 7), the return force of the compressed secondary spring 46 becomes greater than the puncture force of the drive spring 42. At this point, the secondary spring's 46 return force causes the lancet holder 36 to change direction and return to its rest position by moving in the direction of Arrow A. Alternatively, in some embodiments, a stop member may be provided to stop the lancet holder 36 from moving too far in the direction of Arrow B, at which time the secondary spring 46 returns the lancet holder 36 to its rest position.

However, the lancet holder 36 typically moves in the direction of Arrow A further than required to return to its rest position. Thus, slightly recompressing the drive spring 42, which causes the lancet holder 36 to again travel in the direction of Arrow B. As the lancet holder 36 begins to move back in the direction of Arrow B (due to the slight recompression of the drive spring 42), the secondary spring 46 is recompressed. The force required to recompress the secondary spring 46 effectively dampens the movement of the lancet holder 36. Such damping assists in inhibiting or preventing the drive spring 42—and its natural tendency to oscillate (due to its being elastically deformable)—from causing a second, unintended skin puncture.

Turning now to FIG. 8, the pushbutton 22 is illustrated according to one embodiment of the present invention. The pushbutton 22 includes a body 62 from which the two catch arms 52a,b extend. Each of the catch arms 52a,b includes an end 53a,b, respectively, opposite from the body 62. Each end 53a,b is adapted to engage an angled stop member 50a,b of the lancet holder 36. A lancet-release tab 76 extends from the body 62 of the pushbutton 22 in the same direction as the catch arms 52a,b. The lancet-release tab 76 is adapted to extend through a slot 80 (FIG. 9b) formed in the lancet holder 36 when the pushbutton 22 is depressed towards the lancet holder 36. The lancet-release tab 76 is adapted to engage the lancet 30 as will be described further below with respect to FIGS. 10a-c. The body 62 of the pushbutton includes a depression 22a (FIGS. 1 and 8) or tactile features (not shown) to more easily allow a user to engage the pushbutton 22.

Figure 9A:
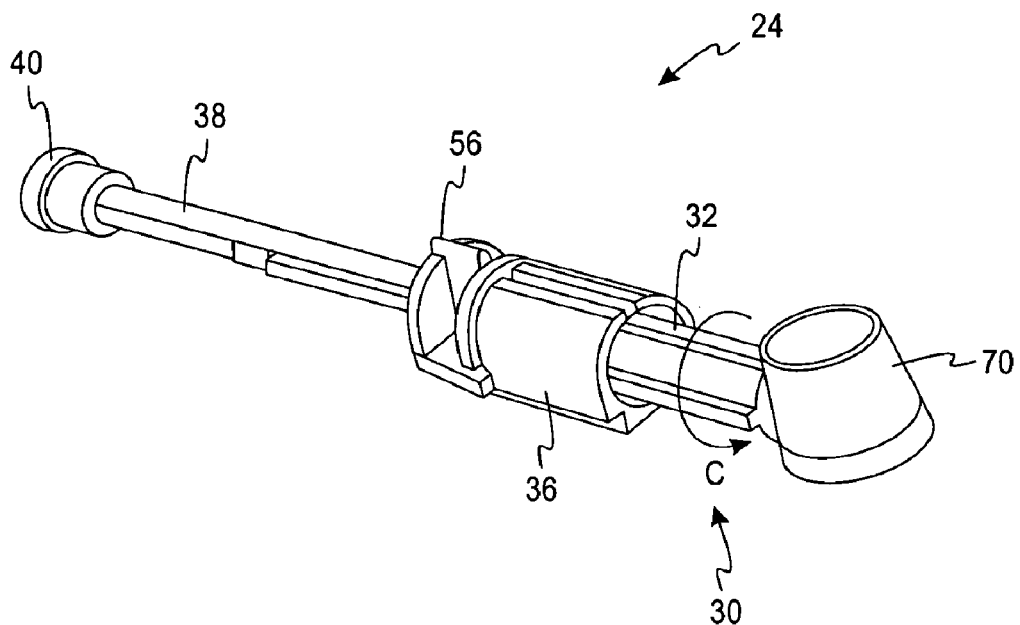
FIGS. 9*a-b* are perspective views of a lancing mechanism, contained within the lancing device of FIG. 1, according to one embodiment of the present invention.
Figure 9B:
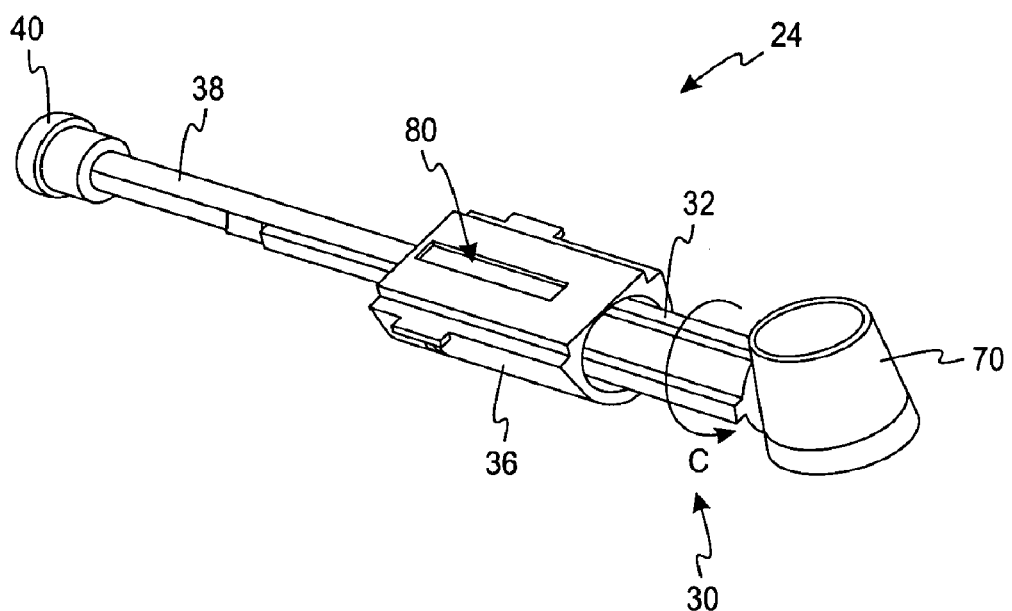

Turning now to FIGS. 9a-b, a perspective view of the lancet 30 disposed within the lancet holder 36 is illustrated. The lancet 30 is shown with the protective cap 70 that has a portion that is integrally formed with the lancet body 32 and which covers the sharp point of the lance 34. Prior to using the lancing device 10, the lancet body 32 of a new lancet 30 is inserted into the cylindrical aperture disposed in the lancet holder 36, and then the protective cap 70 is twisted off of the lancet assembly 30, in the direction of the Arrow C shown in FIG. 9a.

The lancet holder 36 includes the guide rib 56 that is adapted to be inserted into the groove 58 (FIGS. 5-6). The guide rib 56 and groove 58 are adapted to assist in providing a linear puncture of the test subject's skin by the lancet 30. Linear punctures are preferable because they tend to produce a less painful, and faster healing, piercing of the skin.

As best illustrated in FIG. 9b, the lancet holder 36 includes the slot 80 that is adapted to receive the lancet-release tab 76 when the pushbutton 22 is depressed towards the lancet holder 36. The slot 80 allows the lancet-release tab 76 to sufficiently enter the lancet holder 36 that the lancet-release tab 76 is capable or engaging the lancet 30 as will be further described with respect to FIGS. 10a-c.

Figure 10A:
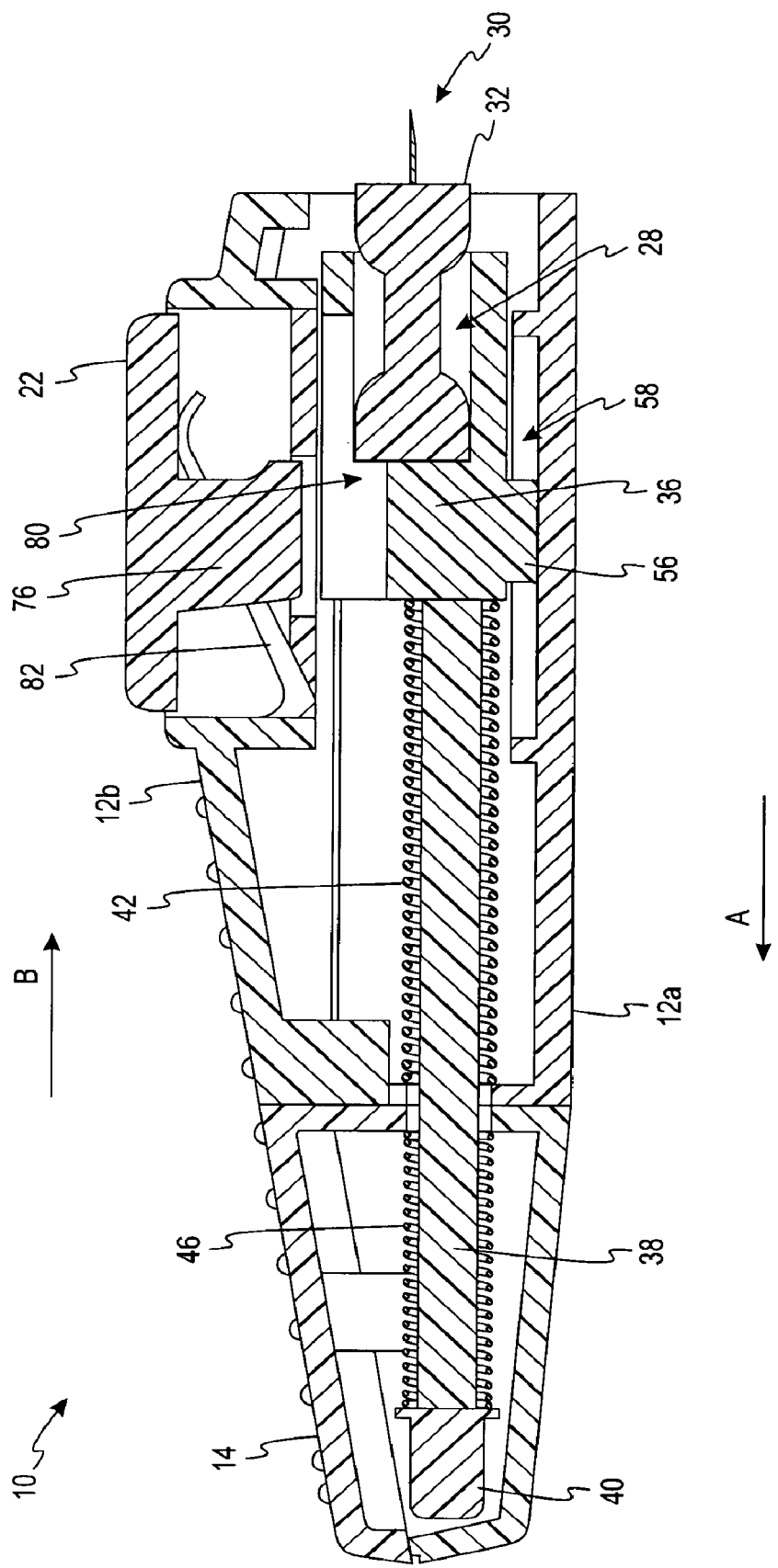
FIG. 10*a* is a cross-sectional side view of the lancing device—taken generally along line 10-10 of FIG. 1—in a cocked position, according to one embodiment of the present invention.
Figure 10B:
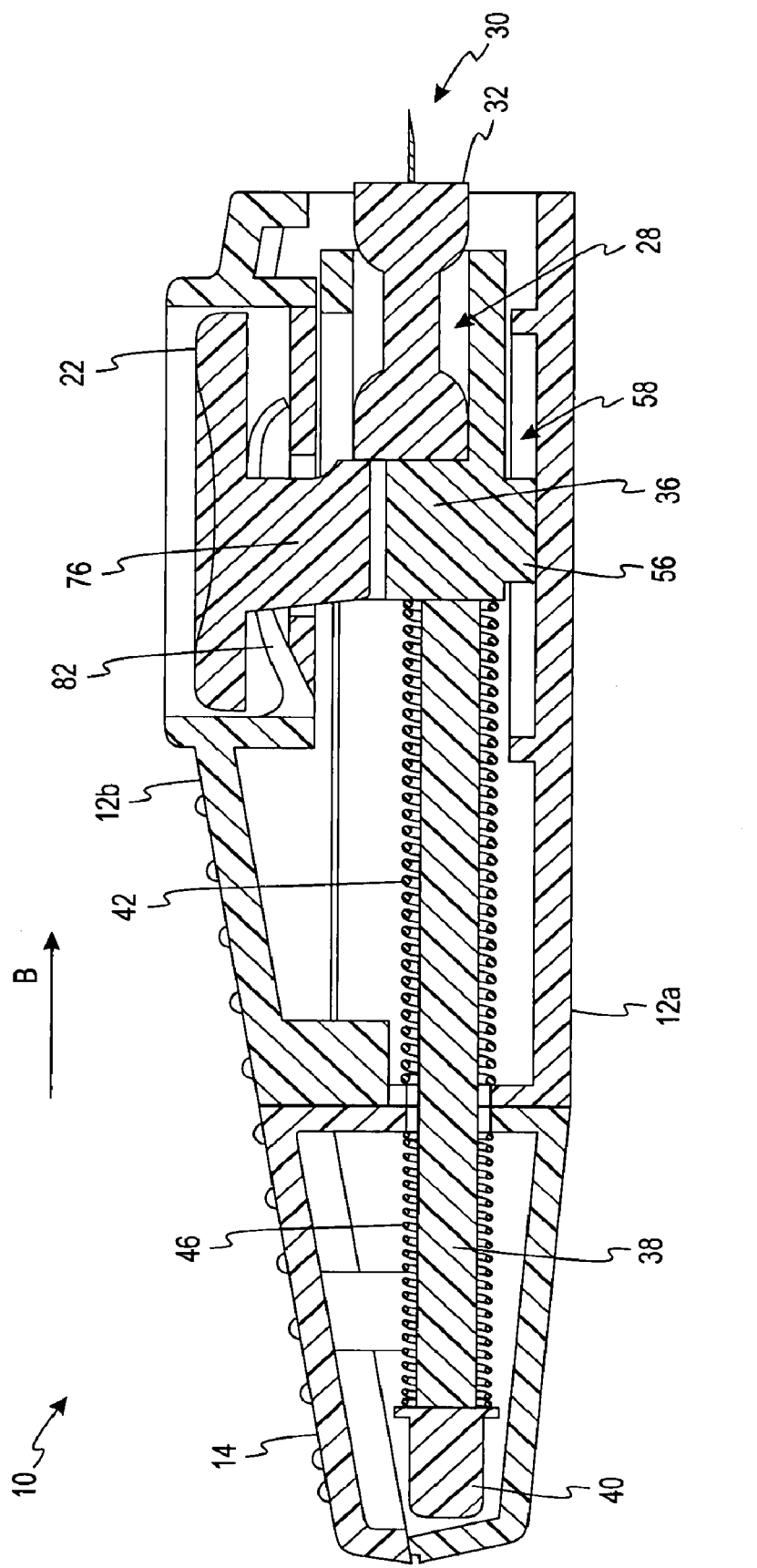
FIG. 10*b* is a cross-sectional side view of the lancing device of FIG. 10*a* in a resting position with a depressed pushbutton.
Figure 10C:
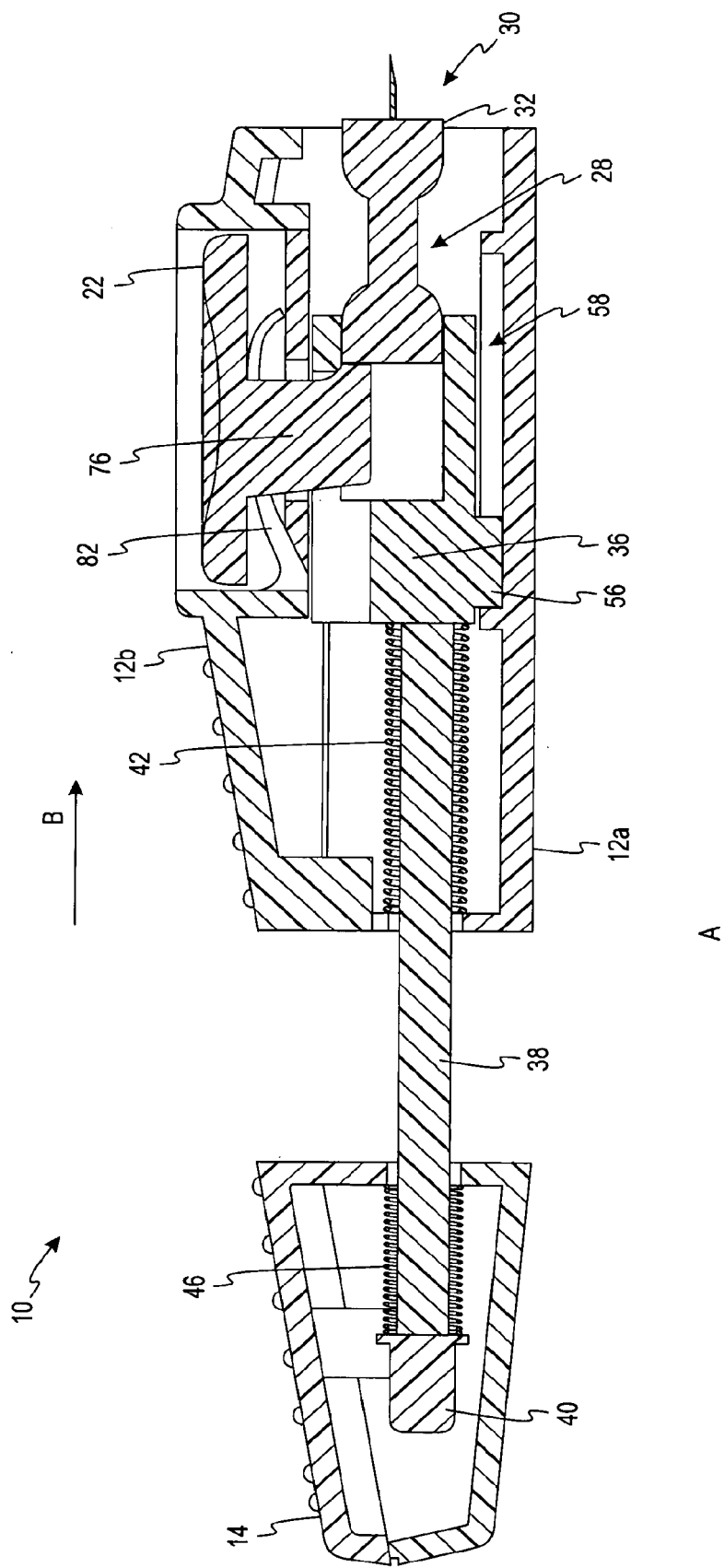
FIG. 10*c* is a cross-sectional side view of the lancing device of FIG. 10*a* in a lancet-release position.

Turning now to FIGS. 10a-c, the release of a lancet 30 from the lancet holder 36 is illustrated, according to one embodiment of the present invention. In FIG. 10a, the lancing device 10 is in its resting position with the drive spring 42 and secondary spring 46 being substantially decompressed. The pushbutton 22 is also in its resting position and, as such, the lancet-release tab 76 does not extend into the slot 80 of the lancet holder 36. Referring now to FIG. 10b, the lancing device 10 remains in its resting position, however, the pushbutton 22 has been depressed in the direction of the lancet holder 36 and the lancet-release tab 76 now extends into the slot 80 of the lancet holder 36. The lancet-release tab 76 extends sufficiently into the lancet holder 36 to engage the lancet 30 received therein—as the lancing device 10 is moved to the lancet-release position illustrated in FIG. 10c.

Referring now to FIG. 10c, the lancing device 10 is illustrated in its lancet-release position. In this position, the pushbutton 22 is sufficiently depressed in the direction of the housing 12 to cause the lancet-release tab 76 to extend through the slot 80 and into the lancet holder 36. Once the pushbutton 22 has been depressed, the movable housing 14 is pulled away from the main housing 12 in the direction of Arrow A. As the movable housing 14 is pulled away from the main housing 12, the lancet holder 36 moves in the direction of Arrow A as well—similar to the movement described above with respect to cocking the lancing device 10.

As the lancet holder 36 moves in the direction of Arrow A, the lancet-release tab 76 engages the lancet 30 and inhibits the lancet 30 from moving in the direction of Arrow A. As the lancet holder 36 continues to move in the direction of Arrow A, the lancet 30 is removed from the lancet holder 36 without the user having to directly contact the lancet 30 with their hand. Once the lancet 30 has been released, the user releases the movable housing 14 and the secondary spring 46 causes the movable housing 14 to move in the direction of Arrow B until the movable housing 14 is once again adjacent the main housing 12.

As should be apparent from the above-described lancet-release mechanism, the potential for unintended punctures to the user is greatly diminished. In addition, the lancet-release mechanism is designed to be easily integrated into existing lancing devices 10 and, because of its unique design, is well-suited to stand the everyday use of a user of the lancing device 10 (e.g., carrying in a purse or pocket, dropping, inadvertent bumping, etc.).

In the above-described lancing device 10, the secondary spring 46 is used to both move the movable housing 14 from the cocking position to the cocked position as well as to return the lancet holder 36 from its puncture position to its rest position. In addition, the secondary spring 46 is adapted to move the movable housing 14 from the lancet-release position to the rest position.

The use of two opposing springs allows for the puncture strength to be adjusted by adjusting the spring ratio between the drive spring 42 and the secondary spring 46, reducing the need to compute the frictional interaction and mass of the various components of the device. Typically, the spring constant of the drive spring 42 is greater than the spring constant of the secondary spring 46, which causes the secondary spring 46 to initially be compressed by the force provided by the drive spring 42.

The structure of the above-described lancing device 10 also allows for both the drive spring 42 and the secondary spring 46 to remain free floating on the shaft 38. Thus, the need for attaching one or both ends of each spring is eliminated, reducing the cost and time required to manufacture the lancing device 10.

Alternative Embodiment A

A lancing device comprising:
 a main housing enclosing a portion of a lancing mechanism, the lancing mechanism including a lancet holder attached to a shaft, the lancet holder being adapted to receive a lancet and having a slot formed therein, the lancing mechanism being adapted to move between a rest position, a cocked position, and a puncture position;
 a movable housing adjacent the main housing, the movable housing being adapted to move from a rest position to a cocking position and a lancet-release position; and
 a pushbutton adapted to allow the lancing mechanism to move from the cocked position to the puncture position upon depression of the pushbutton in the general direction of the main housing, the pushbutton including a lancet-release tab formed thereon, the lancet-release tab being adapted to extend into the slot formed in the lancet holder and engage the lancet,
 wherein the lancet is released from the lancet holder in response to the continued depression of the pushbutton and the movable housing being moved from the rest position to the lancet-release position.

Alternative Embodiment B

The lancing device of Alternative Embodiment A, wherein the pushbutton of the lancet-release mechanism includes a depression that assists a user in engaging the pushbutton.

Alternative Embodiment C

The lancing device of Alternative Embodiment A, wherein the pushbutton of the lancet-release mechanism includes tactile features that assist a user in engaging the pushbutton.

Alternative Embodiment D

The lancing device of Alternative Embodiment A, wherein the lancet-release tab does not engage the lancet until the movable housing is moved from the rest position to the lancet-release position.

Alternative Embodiment E

The lancing device of Alternative Embodiment A, wherein the cocking position and the lancet-release position of the movable housing are substantially identical.

Alternative Process F

A method of releasing a lancet from a lancing device, the method comprising the acts of:
 providing a lancing device including,
  (i) a main housing enclosing a lancet holder being adapted to receive the lancet, the lancet holder having a slot formed therein,
  (ii) a movable housing adjacent the main housing, the movable housing being adapted to move from a rest position to a cocking position and a lancet-release position, and
  (iii) a pushbutton having a lancet-release tab formed thereon, the lancet-release tab being adapted to extend into the slot formed in the lancet holder and engage the lancet;
 depressing the pushbutton in the general direction of the main housing resulting in the lancet-release tab entering the slot formed in the lancet holder; and
 moving the movable housing from the rest position to the lancet-release position, while the pushbutton remains depressed, the moving of the movable housing causing the lancet-release tab to engage the lancet and cause the lancet to release from the lancet holder.

Alternative Process G

The method of Alternative Process F, further comprising the act of removing the lancet from the lancet holder without a user touching the lancet.

Alternative Process H

The method of Alternative Process F, wherein the pushbutton is also adapted to fire the lancing device.

Alternative Process I

The method of Alternative Process H, wherein the pushbutton is utilized to release the lancet from the lancet holder.

Alternative Process J

The method of Alternative Process F, wherein the cocking position and the lancet-release position of the movable housing are substantially identical.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing device comprising:
 a main housing enclosing a portion of a lancing mechanism, the lancing mechanism including a lancet holder attached to a shaft, the lancet holder being adapted to receive a lancet and having a slot formed therein, the lancing mechanism being adapted to move between a rest position, a cocked position, and a puncture position;
 a movable housing adjacent the main housing, the movable housing being adapted to move from a rest position to a cocking position and a lancet-release position; and
 a pushbutton adapted to allow the lancing mechanism to move from the cocked position to the puncture position upon depression of the pushbutton in the general direction of the main housing, the pushbutton including a lancet-release tab formed thereon, the lancet-release tab being adapted to extend into the slot formed in the lancet holder and engage the lancet in response to the depression of the pushbutton,
 wherein the lancet is released from the lancet holder in response to the continued depression of the pushbutton and the movable housing being moved from the rest position to the lancet-release position.

2. The lancing device of claim 1, wherein the pushbutton of the lancet-release mechanism includes a depression that assists a user in engaging the pushbutton.

3. The lancing device of claim 1, wherein the pushbutton of the lancet-release mechanism includes tactile features that assist a user in engaging the pushbutton.

4. The lancing device of claim 1, wherein the lancet-release tab does not engage the lancet until the movable housing is moved from the rest position to the lancet-release position.

5. The lancing device of claim 1, wherein the cocking position and the lancet-release position of the movable housing are substantially identical.

6. A method of releasing a lancet from a lancing device, the method comprising the acts of:
providing a lancing device including,
(i) a main housing enclosing a lancet holder being adapted to receive the lancet, the lancet holder having a slot formed therein,
(ii) a movable housing adjacent the main housing, the movable housing being adapted to move from a rest position to a cocking position and a lancet-release position, and
(iii) a pushbutton having a lancet-release tab formed thereon, the lancet-release tab being adapted to extend into the slot formed in the lancet holder and engage the lancet;
depressing the pushbutton in the general direction of the main housing resulting in the lancet-release tab entering the slot formed in the lancet holder; and
moving the movable housing from the rest position to the lancet-release position, while the pushbutton remains depressed, the moving of the movable housing causing the lancet-release tab to engage the lancet and cause the lancet to release from the lancet holder.

7. The method of claim 6, further comprising the act of removing the lancet from the lancet holder without a user touching the lancet.

8. The method of claim 6, wherein the pushbutton is also adapted to fire the lancing device.

9. The method of claim 8, wherein the pushbutton is utilized to release the lancet from the lancet holder.

10. The method of claim 6, wherein the cocking position and the lancet-release position of the movable housing are substantially identical.

11. A lancing device comprising:
a first housing enclosing at least a portion of a lancing mechanism, the lancing mechanism including a lancet holder configured to receive a lancet and having a slot formed therein, the lancing mechanism configured to move the lancet holder between a rest position, a cocked position, and a puncture position;
a movable housing adjacent the main housing, the movable housing configured to move from a rest position to a cocking position and a lancet-release position; and
a pushbutton configured to release the lancing mechanism thereby allowing the lancet holder to move from the cocked position to the puncture position, the pushbutton including a lancet-release tab formed thereon, the lancet-release tab configured to extend into the slot formed in the lancet holder in response to the depression of the pushbutton,
wherein the lancet is configured to release from the lancet holder in response to continued depression of the pushbutton and the movable housing being moved from the rest position to the lancet-release position.

12. The lancing device of claim 11, wherein the pushbutton of the lancet-release mechanism includes a depression configured to assist a user in engaging the pushbutton.

13. The lancing device of claim 11, wherein the pushbutton of the lancet-release mechanism includes tactile features configured to assist a user in engaging the pushbutton.

14. The lancing device of claim 11, wherein the lancet-release tab is configured to engage the lancet only upon the movable housing being moved from the rest position to the lancet-release position.

15. The lancing device of claim 11, wherein the cocking position and the lancet-release position of the movable housing are substantially identical.

* * * * *